United States Patent [19]

Van der Knaap

[11] Patent Number: Plant 6,302

[45] Date of Patent: Sep. 20, 1988

[54] CHRYSANTHEMUM PLANT NAMED FRANKY LANE

[75] Inventor: Jacques C. M. Van der Knaap, De Lier, Netherlands

[73] Assignee: Fides Beheer B.V., De Lier, Netherlands

[21] Appl. No.: 915,106

[22] Filed: Oct. 3, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Franky Lane particularly characterized by its lavender-pink ray floret color and contrasting disc florets which have an intense red-purple center cushion surrounded by a lavender-pink band; nine week response; anemone capitulum; and, by its excellent flower production.

1 Drawing Sheet

The present invention comprises a new and distinct cultivar of Chrysnthemum, botanically known as *Chrysanthemum morifolium*, Ramat., and referred to by the cultivar name Franky Lane.

Franky Lane was discovered by applicant in 1984 as a spontaneous mutation of Penny Lane, a cultivar of applicant disclosed in a pending application.

Franky Lane was the result of an induced radiation program conducted by applicant in De Lier, The Netherlands, in 1984. Plants of the parent cultivar Penny Lane were subjected to radiation levels of 1750 rad X-rays. Franky Lane was discovered and selected as a mutation by virtue of its lavender-pink ray floret color, and unique disc floret colors. The center cushion is a relatively intense red-purple, encircled by a generally pink band. The disc florets of Penny Lane are dark orange, surrounded by a yellow band, and the ray florets are more pinkish.

The first act of asexual reproduction of Franky Lane was accomplished when vegetative cuttings were taken from the initial selection in 1984 in a controlled environment in De Lier, The Netherlands by a technician working under formulations established and supervised by Jacques C. M. Van der Knaap. Horticultural examination of selected units initiated in 1984 has demonstrated that the combination of characteristics as herein disclosed for Franky Lane are firmly fixed and are retained through successive generations of asexual reproduction.

Franky Lane has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Franky Lane which, in combination, distinguish this Chrysanthemum as a new and distinct cultivar:

1. Anemone capitulum.
2. Lavender-pink ray floret color, with the disc florets comprising an intense red-purple center cushion surrounded by a light pink band.
3. Nine week response.
4. Excellent flower production per stem.

Of the many commercial cultivars known to the present inventor, the most similar in comparison to Franky Lane is the parent cultivar Penny Lane. Except for the differences in ray and disc floret colors noted above, the cultivars have very similar characteristics.

The accompanying photographic drawing shows typical inflorescence and foliage characteristics of Franky Lane, with colors being depicted as accurately as possible with photographs of this type.

In the following description, color references are made to The Royal Horticultural Society Colour Chart. The color values were determined between 11:00 a.m. and 12:00 noon in August 1986 under natural daylight at De Lier, The Netherlands.

Classification:

*Botanical.*—*Chrysanthemum morifolium*, Ramat., cv. Franky Lane.

*Commercial.*—Anemone spray.

INFLORESCENCE

A. Capitulum:
- *Form.*—Flat.
- *Type.*—Anemone.
- *Diameter across face.*—30–55 mm.

B. Corollas of ray florets:
- *Color (general tonality from a distance of three meters).*—Lavender-pink.
- *Color (upper surface).*—65D.
- *Color (under surface).*—65D.

C. Corolla of disc florets:
- *Color (mature).*—Intense red-purple 64C-D in center, with peripheral band of 65C lavender-pink.

D. Reproductive organs:
- *Androecium.*—Present in disc florets.
- *Gynoecium.*—Present in both ray and disc florets.

PLANT

A. General appearance:
- *Height.*—75cm.

B. Foliage:
- *Color (upper surface).*—147A.
- *Color (under surface).*—147B.
- *Shape.*—Lobed and serrated.

I claim:

1. A new and distinct Chrysanthemum plant named Franky Lane, as described and illustrated, and particularly characterized by its lavender-pink ray floret color and contrasting disc florets which have an intense red-purple center cushion surrounded by a lavender-pink band; nine week response; anemone capitulum; and, excellent flower production.

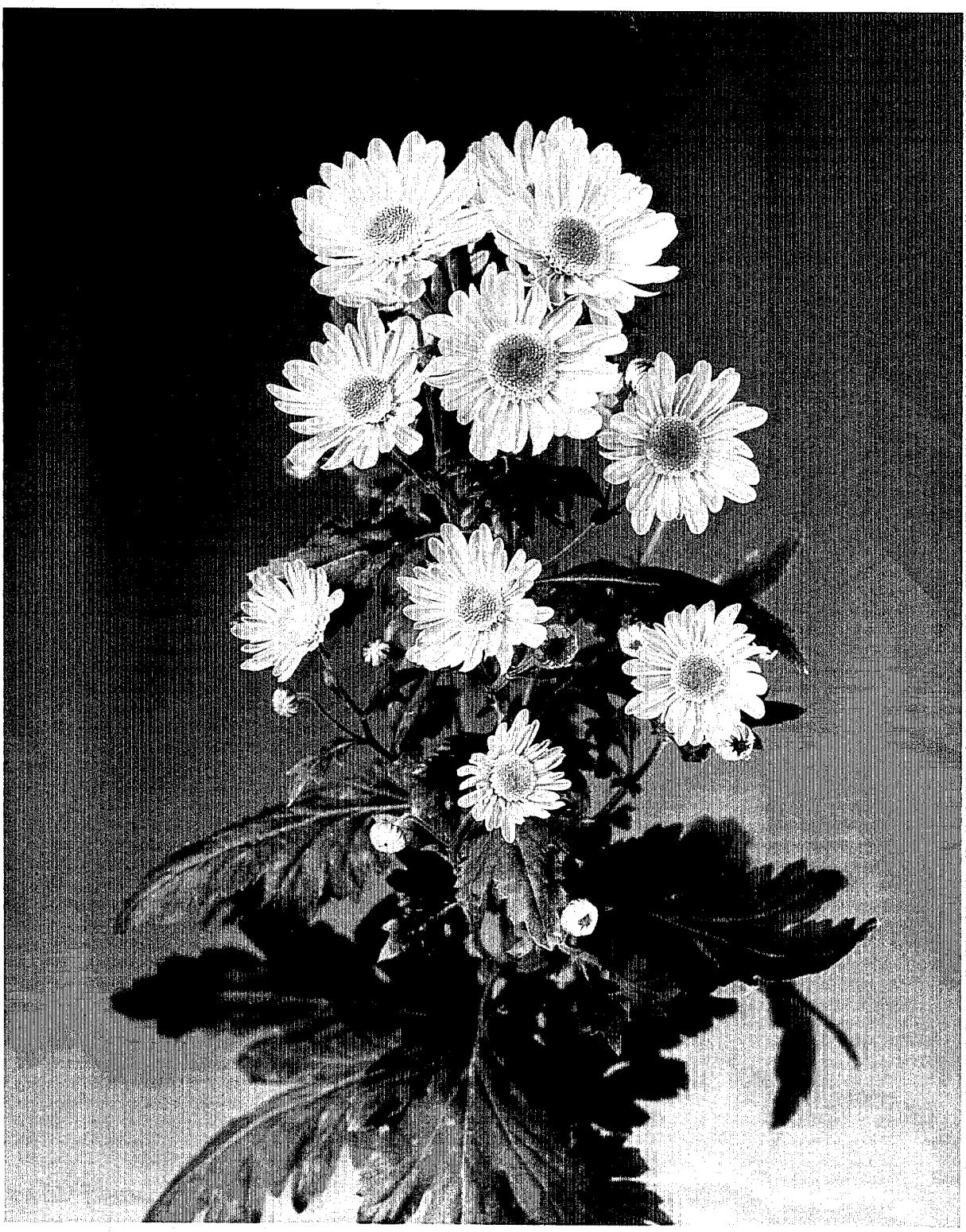

* * * * *